US00PP23180P3

(12) United States Plant Patent
Korlipara

(10) Patent No.: US PP23,180 P3
(45) Date of Patent: Nov. 13, 2012

(54) ***NEPETA* PLANT NAMED 'PURPLE HAZE'**

(50) Latin Name: ***Nepeta* spp.**
Varietal Denomination: Purple Haze

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 66 days.

(21) Appl. No.: 12/930,876

(22) Filed: Jan. 19, 2011

(65) Prior Publication Data

US 2012/0185980 P1 Jul. 19, 2012

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu

(74) *Attorney, Agent, or Firm* — Jondle & Associates, P.C.

(57) ABSTRACT

A new and distinct form of *Nepeta* plant characterized by very long inflorescences with densely packed violet flowers, a decumbent, well branched habit, an extremely long bloom time, clean-looking, grey green, pubescent foliage, and excellent vigor.

1 Drawing Sheet

Botanical denomination: *Nepeta* spp.
Variety designation: 'Purple Haze'.

BACKGROUND OF THE INVENTION

The present invention relates to a new and distinct cultivar of *Nepeta*, given the name, 'Purple Haze'. *Nepeta* is in the family Lamiaceae. This plant originated from a planned breeding cross between *Nepeta tuberosa*, as the seed parent, and *Nepeta govaniana*, as the pollen parent. This cultivar was selected for its low growing habit, long flowering time, long, dense, purple blue inflorescences, and clean attractive look. It is an ideal plant for a sunny border in full sun. There are no similar cultivars on the market.

Compared to the seed parent, *Nepeta tuberosa*, an unpatented plant, the new cultivar has much longer bloom time, longer inflorescences, more stems from the crown, and a more spreading habit.

Compared to the pollen parent, *Nepeta govaniana*, an unpatented plant, the new cultivar is spreading rather than upright and has violet flowers rather than white.

*Nepeta* 'Purple Haze' is uniquely distinguished by:

1. very long inflorescences with densely packed violet flowers,
2. decumbent, well branched habit,
3. extremely long bloom time,
4. clean-looking, grey green, pubescent foliage, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one year old *Nepeta* Purple Haze growing in a hanging basket in the summer in Canby, Oreg.

FIG. 2 shows a two year old *Nepeta* 'Purple Haze' in bloom growing in full sun in the trial bed in May in Canby, Oreg.

DETAILED PLANT DESCRIPTION

The following is a detailed description of the new *Nepeta* cultivar based on observations of a two-year-old specimen grown outside in the ground in the trial beds in Canby, Oreg. in May. The color descriptions are all based on The Royal Horticultural Society Colour Chart, $5^{th}$ edition.

Plant:

*Type*.—Herbaceous perennial.
*Form*.—Decumbent, clumping ground cover.
*Cold Hardiness*.—USDA Zone 6-10.
*Size*.—Grows to 64 cm wide and 28 cm high.
*Vigor*.—Excellent.
*Stem number*.—12 stems from the crown.
*Stem*.—Decumbent, grows to 22 cm long and 5 mm wide (at the base), internodes grow to 5 cm long, pubescent, Yellow Green 147D tinted Greyed Purple 187B in sun, square in cross section.
*Rooting*.—Plants root easily from stem cuttings.

Leaf:

*Type*.—Simple, aromatic.
*Arrangement*.—Opposite.
*Shape*.—Ovate.
*Venation*.—Pinnate.
*Margins*.—Crenate.
*Apex*.—Obtuse.
*Base*.—Auriculate, clasping on upper leaves.
*Blade size*.—Grows to 5 cm long and 2.7 cm wide.
*Surface texture*.—Pubescent on both sides.
*Petiole*.—On basal leaves, grows to 8 mm, pubescent, Green N138C.
*Leaf color*.—Topside Green N138B, bottom side Green N138C.

Inflorescence:

*Type*.—Terminal many flowered dense verticillaster in opposite stalked to sessile cymes.

*Number of flowers*.—Opposite cymes in up to 18 rings of 9 to 40 flowers per cyme.

*Size of inflorescence*.—Grows to 42 cm long and 5.5 cm wide.

*Peduncle*.—Grows to 10 cm long and 5 mm wide, pubescent, Yellow Green 147D tinted Greyed Purple 187B in sun.

*Pedicel*.—Sessile.

*Bloom period*.—April to October in Canby, Oreg.

Flower bud:

*Size*.—10 mm long and 3 mm wide at the widest point prior to opening.

*Description*.—Irregular teardrop, flattened dorsally.

*Surface*.—Pubescent.

*Color*.—Violet Blue 90B.

Flower:

*Type*.—Zygomorphic, hermaphroditic.

*Shape*.—Bilabiate.

*Corolla description*.—12 mm long and to 9 mm wide; pubescent outside and glabrous inside with hairs lining inside of the throat; tube 5 mm long and Violet Blue 97D; throat Violet 86D on outside, inside Violet 85D with small and large spots of Violet 86A, 3 mm long and 2 mm wide, flattened dorsally; upper lip 2.5 mm wide and 3 mm long, two lobed, reflexed, Violet 86D inside and out; lower lip 5 mm wide and 7 mm long, slightly cupped, Violet 86D on the two lateral lobes and Violet 86B on the larger lower lobe inside and out.

*Calyx description*.—Funnel form, 5 lobed, 9 mm long and 2 mm wide, lobes narrow, tips acuminate, margin entire, villous outside, glabrous inside, Yellow Green 147C at base to lobes Greyed Purple 187A.

*Pistil description*.—1, 11 mm long, ovary 1 mm long and Yellow Green 147D; style 10 mm long, Blue Violet 91C at base to Violet 86C at stigma, stigma Violet 86A.

*Stamen description*.—4, sterile, filaments 2 mm long and Violet 85C, anthers 1 mm long and Greyed Brown 199D, pollen none.

*Fragrance*.—Slight.

*Lastingness*.—A spike blooms for about 6 weeks on the plant.

Fruit and seed: None.

Pests and diseases: *Nepeta* are known to be susceptible to southern blight and various fungal leaf spots, crown rot, and fungal root rot. The new cultivar has shown no problems in Canby, Oreg.

I claim:

1. A new and distinct form of *Nepeta* plant substantially as shown and described.

* * * * *

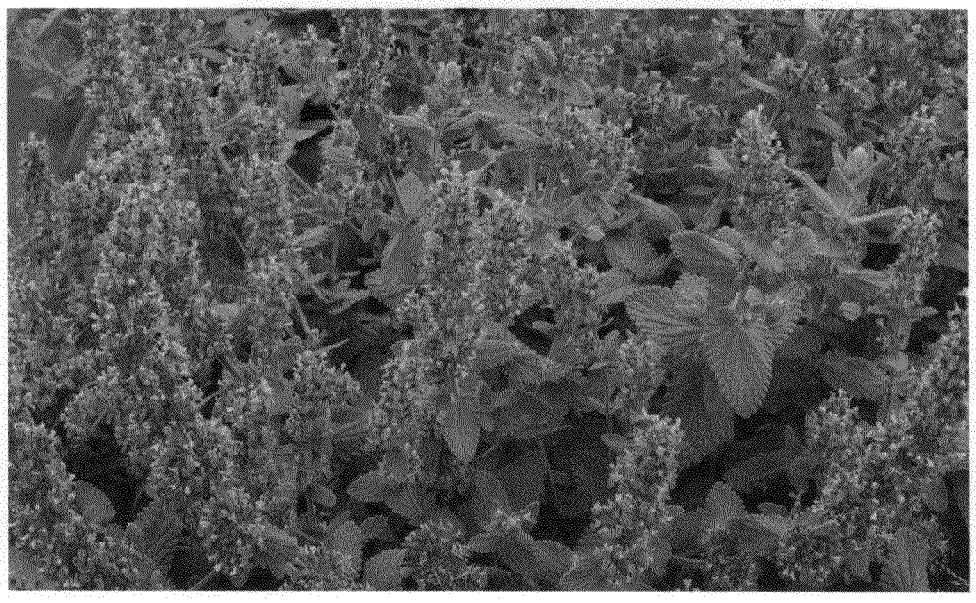

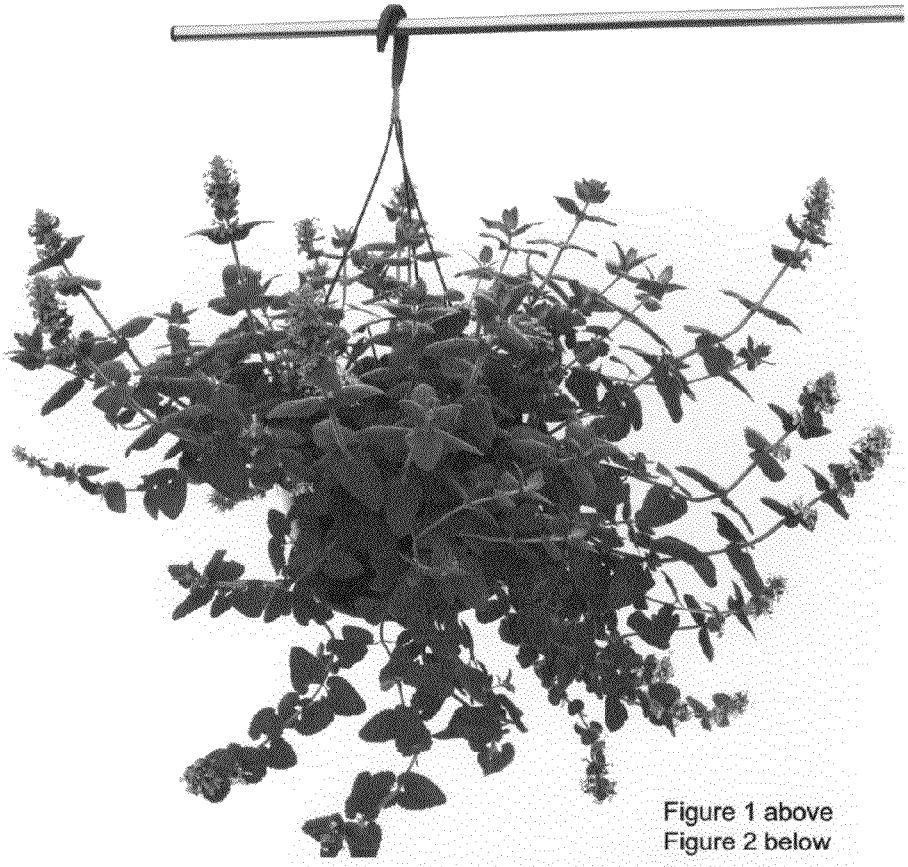
Figure 1 above
Figure 2 below